(12) United States Patent
Michaud

(10) Patent No.: US 12,233,240 B2
(45) Date of Patent: Feb. 25, 2025

(54) METHODS OF WIRELESS COMMUNICATION IN AN INFUSION PUMP SYSTEM

(71) Applicant: Tandem Diabetes Care, Inc., San Diego, CA (US)

(72) Inventor: Michael Michaud, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 603 days.

(21) Appl. No.: 16/725,337

(22) Filed: Dec. 23, 2019

(65) Prior Publication Data

US 2020/0206420 A1 Jul. 2, 2020

Related U.S. Application Data

(60) Provisional application No. 62/784,939, filed on Dec. 26, 2018.

(51) Int. Cl.
*G16H 40/67* (2018.01)
*A61M 5/172* (2006.01)
*G16H 20/17* (2018.01)

(52) U.S. Cl.
CPC .......... *A61M 5/1723* (2013.01); *G16H 20/17* (2018.01); *G16H 40/67* (2018.01);
(Continued)

(58) Field of Classification Search
CPC ............ A61M 5/1723; A61M 2205/18; A61M 2205/3561; A61M 2205/3584; A61M 2205/50; A61M 2205/505; A61M 2205/52; A61M 2205/581; A61M 2230/201; A61M 5/00; A61M 2005/006; A61M 5/001; A61M 5/002; A61M 5/007; A61M 5/008; A61M 5/14; A61M 5/178; A61M 5/36; A61M 5/42; A61M 5/44; A61M 5/46; A61M 5/48; A61M 5/50; A61M 5/52;
(Continued)

(56) References Cited

U.S. PATENT DOCUMENTS 6,024,699 A 2/2000 Surwit et al.
6,553,244 B2 4/2003 Lesho et al.
(Continued)

FOREIGN PATENT DOCUMENTS

| CN | 204951875 U | * | 1/2016 |
| EP | 3223689 A2 | | 10/2017 |
| JP | 2013081128 A | * | 5/2013 |

*Primary Examiner* — James J Yang
*Assistant Examiner* — Anthony D Afrifa-Kyei
(74) *Attorney, Agent, or Firm* — Morgan, Lewis & Bockius LLP

(57) ABSTRACT

Disclosed herein are methods for establishing communication protocols between wireless devices in infusion pump systems. Infusion pump systems can include a number of components capable of wireless communication with one or more other components including an infusion pump, a continuous glucose monitoring (CGM) system, a smartphone or other remote consumer electronic device and/or a dedicated remote controller for the infusion pump. In order to ensure reliable communication of data, more than one component in a system can be capable of relaying data to another component.

18 Claims, 9 Drawing Sheets

(52) U.S. Cl.
CPC . *A61M 2205/18* (2013.01); *A61M 2205/3561* (2013.01); *A61M 2205/3584* (2013.01); *A61M 2205/50* (2013.01); *A61M 2205/505* (2013.01); *A61M 2205/52* (2013.01); *A61M 2205/581* (2013.01); *A61M 2230/201* (2013.01)

(58) Field of Classification Search
CPC .... A61M 2205/3592; A61M 2205/502; A61M 2205/582; A61M 5/14248; G16H 20/17; G16H 40/67
See application file for complete search history.

(56) References Cited

U.S. PATENT DOCUMENTS

| | | | |
|---|---|---|---|
| 6,641,533 B2 | 11/2003 | Causey, III et al. |
| 6,649,403 B1 | 11/2003 | Mcdevitt et al. |
| 6,780,156 B2 | 8/2004 | Haueter et al. |
| 6,790,198 B1 | 9/2004 | White |
| 6,821,249 B2 | 11/2004 | Casscells, III et al. |
| 6,882,940 B2 | 4/2005 | Potts et al. |
| 7,181,505 B2 | 2/2007 | Haller et al. |
| 7,316,899 B2 | 1/2008 | Mcdevitt et al. |
| 7,558,629 B2 | 7/2009 | Keimel et al. |
| 7,594,889 B2 | 9/2009 | St. Ores et al. |
| 7,811,279 B2 | 10/2010 | John |
| 7,860,583 B2 | 12/2010 | Condurso et al. |
| 7,931,613 B2 | 4/2011 | Haueter et al. |
| 7,972,296 B2 | 7/2011 | Braig et al. |
| 8,002,700 B2 | 8/2011 | Ferek-Petric et al. |
| 8,094,009 B2 | 1/2012 | Allen et al. |
| 8,123,720 B2 | 2/2012 | Solomon |
| 8,130,095 B2 | 3/2012 | Allen et al. |
| 8,226,558 B2 | 7/2012 | Say et al. |
| 8,234,128 B2 | 7/2012 | Martucci et al. |
| 8,269,634 B2 | 9/2012 | Fischell et al. |
| 8,287,454 B2 | 10/2012 | Wolpert et al. |
| 8,287,495 B2 | 10/2012 | Michaud et al. |
| 8,313,433 B2 | 11/2012 | Cohen |
| 8,323,188 B2 | 12/2012 | Tran |
| 8,340,792 B2 | 12/2012 | Condurso et al. |
| 8,344,847 B2 | 1/2013 | Moberg et al. |
| 8,414,563 B2 | 4/2013 | Kamen et al. |
| 8,449,524 B2 | 5/2013 | Braig et al. |
| 8,573,027 B2 | 11/2013 | Rosinko et al. |
| 8,712,748 B2 | 4/2014 | Thukral |
| 8,818,782 B2 | 8/2014 | Thukral |
| 8,986,253 B2 | 3/2015 | DiPerna |
| 9,065,720 B2 | 6/2015 | Allen |
| 9,381,297 B2 | 7/2016 | Brown et al. |
| 9,474,856 B2 | 10/2016 | Blomquist |
| 9,483,615 B2 | 11/2016 | Roberts |
| 9,486,571 B2 | 11/2016 | Rosinko |
| 9,555,186 B2 | 1/2017 | Kruse |
| 9,565,718 B2 | 2/2017 | Swanson |
| 9,675,756 B2 | 6/2017 | Kamen |
| 9,737,656 B2 | 8/2017 | Rosinko |
| 9,750,873 B2 | 9/2017 | Brown et al. |
| 9,993,595 B2 | 6/2018 | Michaud et al. |
| 10,213,547 B2 | 2/2019 | Rosinko |
| 10,279,106 B1 | 5/2019 | Cook et al. |
| 10,279,107 B2 | 5/2019 | Michaud |
| 10,430,043 B2 | 10/2019 | Rosinko et al. |
| 10,478,551 B2 | 11/2019 | Rosinko |
| 10,492,141 B2 | 11/2019 | Kruse |
| 10,736,037 B2 | 8/2020 | Kruse et al. |
| 10,773,015 B2 | 9/2020 | Blomquist et al. |
| 10,806,851 B2 | 10/2020 | Rosinko |
| 10,888,655 B2 | 1/2021 | Farnan et al. |
| 2002/0002326 A1 | 1/2002 | Causey, III |
| 2004/0073095 A1 | 4/2004 | Causey et al. |
| 2004/0172222 A1 | 9/2004 | Simpson |
| 2004/0176984 A1 | 9/2004 | White |
| 2005/0277912 A1 | 12/2005 | John |
| 2006/0031094 A1 | 2/2006 | Cohen et al. |
| 2007/0016449 A1 | 1/2007 | Cohen et al. |
| 2007/0033074 A1 | 2/2007 | Nitzan et al. |
| 2007/0156033 A1 | 7/2007 | Causey, III et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255116 A1 | 11/2007 | Mehta et al. |
| 2007/0258395 A1 | 11/2007 | Jollota et al. |
| 2008/0071580 A1 | 3/2008 | Marcus et al. |
| 2008/0294024 A1 | 11/2008 | Cosentino |
| 2009/0006061 A1 | 1/2009 | Thukral |
| 2009/0006129 A1 | 1/2009 | Thukral |
| 2009/0018779 A1 | 1/2009 | Cohen et al. |
| 2009/0030733 A1 | 1/2009 | Cohen et al. |
| 2009/0058635 A1 | 3/2009 | Lalonde |
| 2009/0099866 A1 | 4/2009 | Newman |
| 2009/0099867 A1 | 4/2009 | Newman |
| 2009/0150186 A1 | 6/2009 | Cohen et al. |
| 2009/0150484 A1 | 6/2009 | Roberts |
| 2009/0156991 A1 | 6/2009 | Roberts |
| 2009/0157202 A1 | 6/2009 | Roberts et al. |
| 2009/0157622 A1 | 6/2009 | Roberts et al. |
| 2009/0157695 A1 | 6/2009 | Roberts |
| 2009/0158274 A1 | 6/2009 | Roberts |
| 2009/0177248 A1 | 7/2009 | Roberts |
| 2009/0177249 A1 | 7/2009 | Roberts et al. |
| 2009/0177769 A1 | 7/2009 | Roberts |
| 2010/0094110 A1 | 4/2010 | Heller |
| 2010/0121170 A1 | 5/2010 | Rule |
| 2010/0165795 A1 | 7/2010 | Elder et al. |
| 2010/0198183 A1 | 8/2010 | Lanigan et al. |
| 2010/0262434 A1 | 10/2010 | Shaya |
| 2010/0274592 A1 | 10/2010 | Nitzan et al. |
| 2010/0286563 A1 | 11/2010 | Bryer et al. |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0110281 A1 | 5/2011 | Mehta |
| 2011/0149759 A1* | 6/2011 | Jollota ................ H04W 72/02 370/252 |
| 2011/0152970 A1 | 6/2011 | Jollota et al. |
| 2011/0190694 A1 | 8/2011 | Lanier, Jr. et al. |
| 2012/0016305 A1 | 1/2012 | Jollota |
| 2012/0059673 A1 | 3/2012 | Cohen et al. |
| 2012/0078067 A1 | 3/2012 | Kovatchev |
| 2012/0095315 A1 | 4/2012 | Tenbarge et al. |
| 2012/0185267 A1 | 7/2012 | Kamen et al. |
| 2012/0216297 A1 | 8/2012 | Cohen |
| 2013/0053816 A1 | 2/2013 | DiPerna et al. |
| 2013/0345625 A1 | 12/2013 | Causey, III |
| 2014/0054883 A1 | 2/2014 | Lanigan et al. |
| 2015/0011970 A1* | 1/2015 | Kamen ................ G16H 10/65 604/151 |
| 2015/0045641 A1 | 2/2015 | Rule |
| 2015/0174320 A1 | 6/2015 | Grant |
| 2015/0190098 A1 | 7/2015 | Patek |
| 2016/0228041 A1 | 8/2016 | Heller |
| 2016/0256087 A1* | 9/2016 | Doyle, III ............. A61B 5/725 |
| 2016/0271325 A1 | 9/2016 | Farnan |
| 2016/0328991 A1 | 11/2016 | Simpson |
| 2017/0351842 A1 | 5/2017 | Booth |
| 2018/0289891 A1* | 10/2018 | Finan .................... G16H 40/63 |
| 2019/0167902 A1 | 2/2019 | Kamen |
| 2019/0298915 A1 | 10/2019 | Rosinko |
| 2019/0307952 A1 | 10/2019 | Butler et al. |
| 2019/0321545 A1 | 10/2019 | Rosinko |
| 2019/0321552 A1 | 10/2019 | DiPerna et al. |
| 2020/0009319 A1 | 1/2020 | Ludolph |
| 2020/0009320 A1 | 1/2020 | Ludolph |
| 2020/0077340 A1 | 3/2020 | Kruse |
| 2020/0329433 A1 | 10/2020 | Kruse et al. |

\* cited by examiner

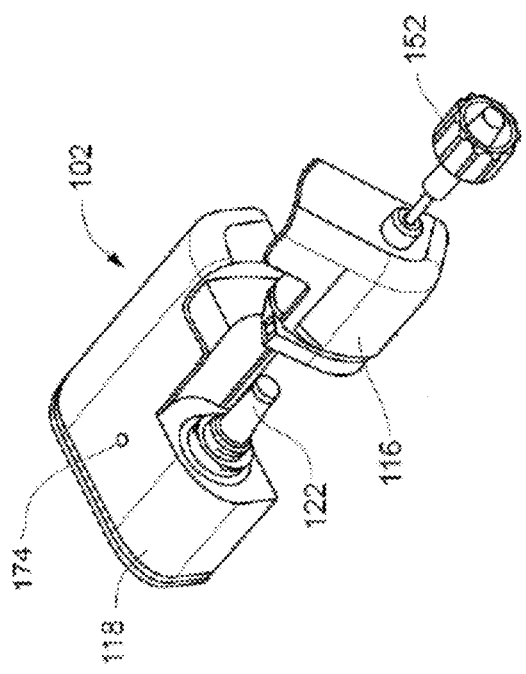
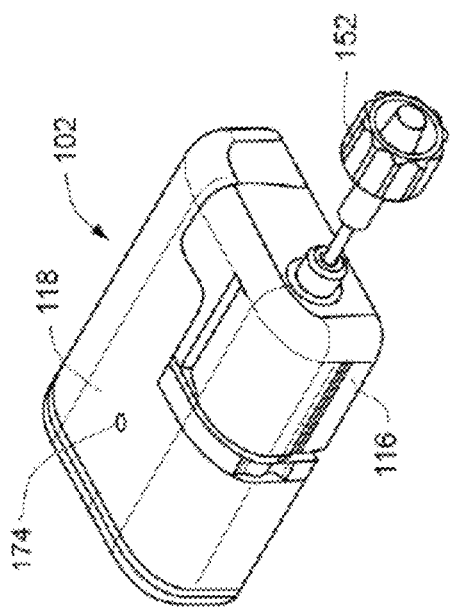
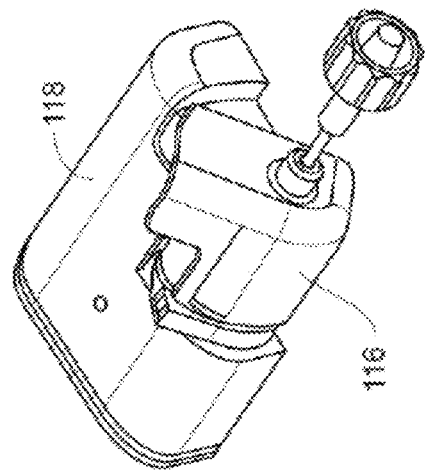

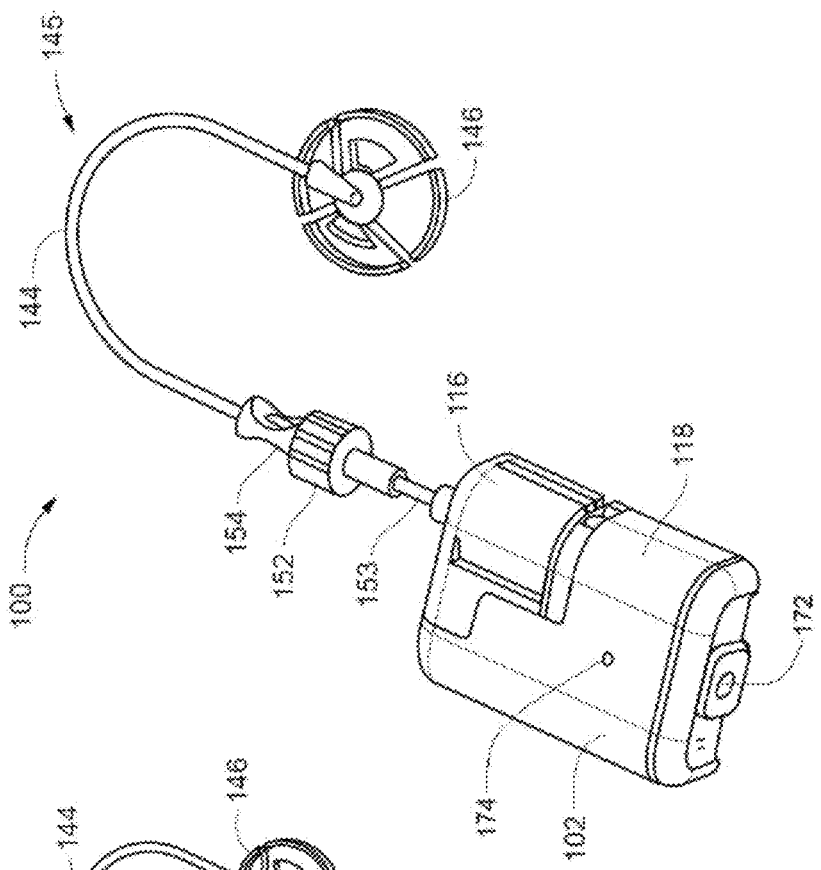
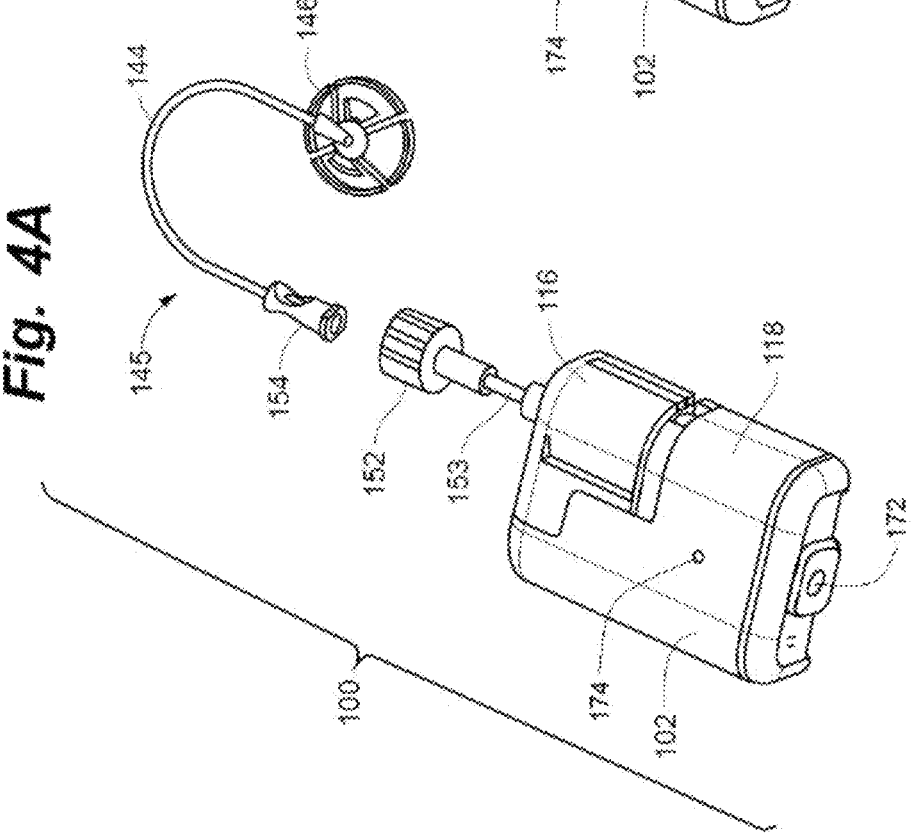

METHODS OF WIRELESS COMMUNICATION IN AN INFUSION PUMP SYSTEM

RELATED APPLICATION

The present application claims the benefit of U.S. Provisional Application No. 62/784,939 filed Dec. 26, 2018, which is hereby incorporated herein in its entirety by reference.

TECHNICAL FIELD

The present invention is directed to portable infusion pumps and more particularly to wireless communications of infusion pumps.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps have generally been controlled by a user interface provided on the pump. With the proliferation of handheld electronic devices, such as mobile phones (e.g., smartphones), there is a desire to be able to remotely utilize such devices, as well as dedicated wireless controllers designed to work with one or more infusion pumps and/or types of infusion pumps, to optimize usage of infusion pumps. These remote controllers would enable a pump to be monitored, programmed and/or operated more privately, more conveniently and more comfortably. Accordingly, one potential use of dedicated remote devices and handheld consumer electronic devices (such as smartphones, tablets and the like) is to utilize such devices as controllers for remotely programming and/or operating infusion pumps.

In addition to mobile control devices such as smartphones and dedicated remote controllers it may be beneficial to enable infusion pumps to communicate with other devices, such as continuous glucose monitors, glucose meters, and other health monitoring devices, for example. However, wireless communications are subject to interference for a number of reasons and therefore relying on wireless communication for medical therapy may pose some disadvantages as well. It would therefore be desirable to configure such communications to reduce the risk of important medical data not being transmitted due to communication issues.

SUMMARY

Disclosed herein are methods for establishing communication protocols between wireless devices in infusion pump systems. Infusion pump systems can include a number of components capable of wireless communication with one or more other components including an infusion pump, a continuous glucose monitoring (CGM) system, a smartphone or other remote consumer electronic device and/or a dedicated remote controller for the infusion pump. In order to ensure reliable communication of data, more than one component in a system can be capable of relaying data to another component.

In one embodiment, methods of communication in an infusion pump system in which an infusion pump can communicate with both a remote control device and a continuous glucose monitor (CGM) sensor/transmitter include use of the remote control device as a relay device if communications between the infusion pump and the CGM transmitter are disrupted. During standard operation, the CGM transmitter directly sends data obtained by the CGM sensor to the pump for use in therapy determinations by the pump. However, if the pump becomes unable to receive the CGM data, rather than the pump operating without the data the remote control device can receive the data from the CGM transmitter and relay the data to the pump for use by the pump.

In an embodiment, a method of coordinating wireless communications in an infusion pump system including an infusion pump, a remote control device for remotely controlling the infusion pump, and a continuous glucose monitoring system is provided. Initially, communications are established between the infusion pump and the CGM system to enable the CGM system to transmit CGM data to the infusion pump and the infusion pump can determine therapy parameters utilizing the CGM data. If it is determined that the infusion pump is no longer receiving the CGM data communicated by the CGM system, the CGM data can be received from the CGM system at the remote control device. The remote control device can then relay the CGM data from the CGM system to the infusion pump to enable the infusion pump to continue to determine therapy parameters utilizing the CGM data even though the infusion pump is not receiving the CGM data from the CGM system itself.

In an embodiment, a method of coordinating wireless communications in an infusion pump system including an infusion pump, a remote control device for remotely controlling the infusion pump, and a CGM system is provided. A connection between the infusion pump and the CGM system is monitored to determine whether the infusion pump is receiving CGM data from the CGM system. If it is determined that the infusion pump is not receiving the CGM data from the CGM system, then the CGM data is received from the CGM system at another device and relayed from the CGM system to the infusion pump via the other device.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 3A-3C depicts an embodiment of a pump system according to the disclosure.

FIGS. 4A-4B depict an embodiment of a pump system according to the disclosure.

Figure 1:
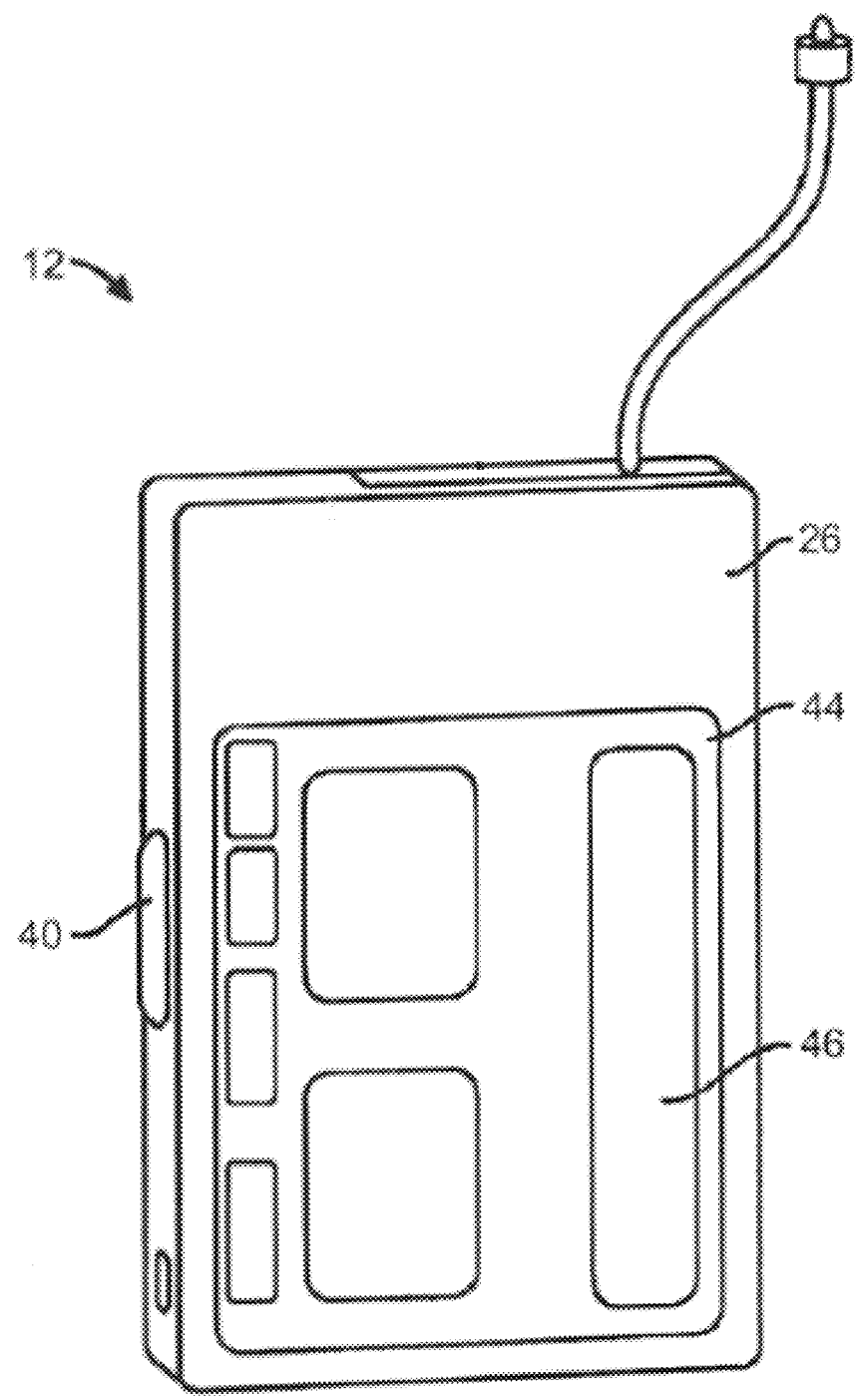
FIG. 1 depicts an embodiment of a pump system according to the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

FIG. 1 depicts an exemplary medical device that can be used with embodiments of the disclosure. In this embodiment, the medical device is configured as a pump 12, such as an infusion pump, that can include a pumping or delivery mechanism and reservoir for delivering medicament to a patient and an output/display 44. The type of output/display 44 may vary as may be useful for a particular application. The output/display 44 may include an interactive and/or touch sensitive screen 46 having an input device such as, for example, a touch screen comprising a capacitive screen or a resistive screen. The pump 12 may additionally include a keyboard, microphone, or other input device known in the art for data entry, which may be separate from the display. The pump 12 may also include a capability to operatively couple to one or more blood glucose meters (BGMs) or continuous blood glucose monitors (CGMs) and/or one or more secondary display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be a portable pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient.

Figure 2:
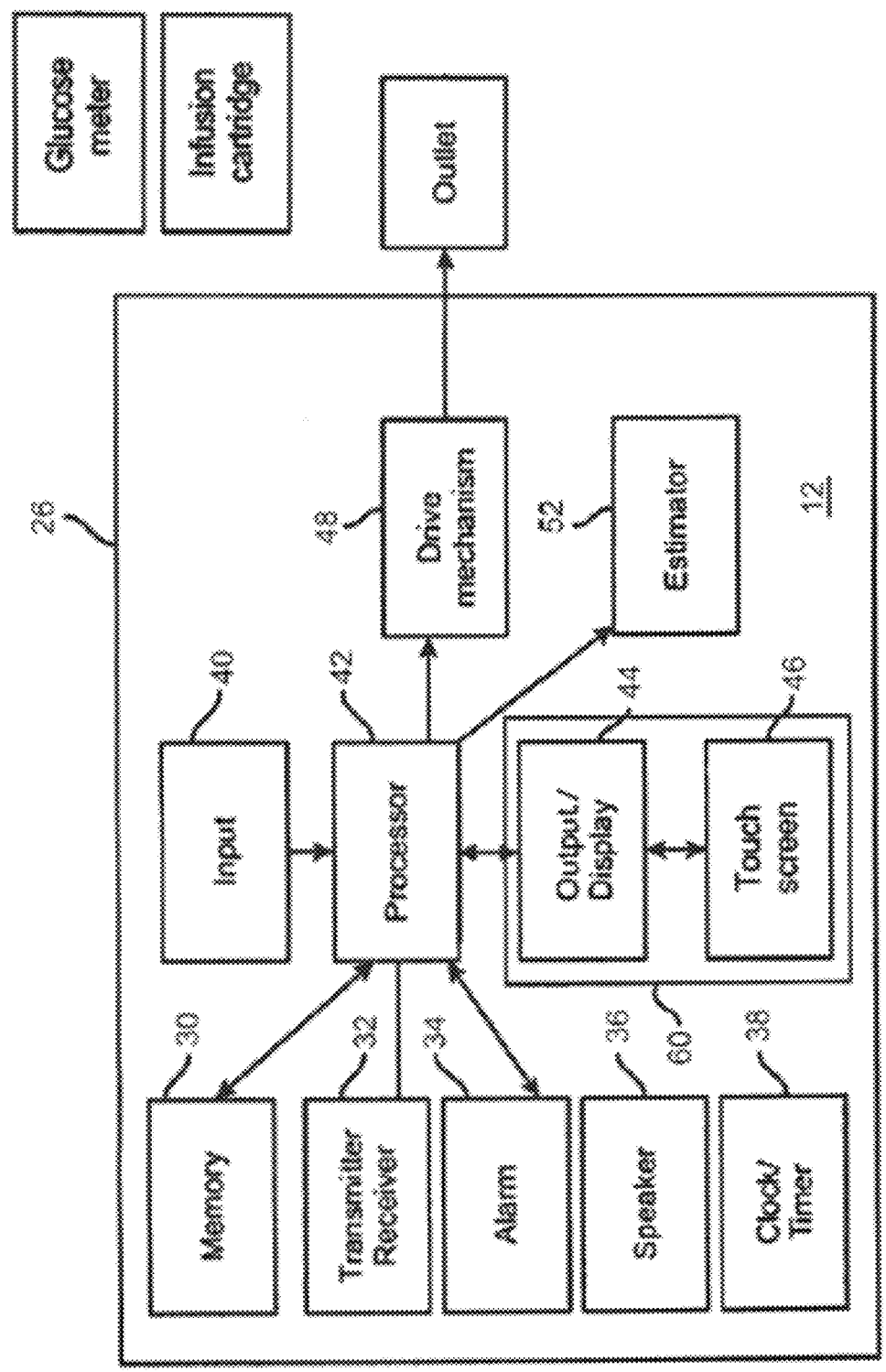
FIG. 2 depicts a block diagram representing an embodiment of a pump system according to the disclosure.

FIG. 2 illustrates a block diagram of some of the features that can be used with embodiments, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface as shown in FIG. 2 is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from one or more input devices, such as sensors that may sense pressure, temperature and/or other parameters.

FIGS. 3A-3C depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118 and provide for delivery of medicament such as insulin from the cartridge 116 to a user through a cannula. Further details regarding such pumps can be found in U.S. patent application Ser. No. 14/707,851 filed May 8, 2015 and U.S. Patent Publication Nos. 2016/0339172 and 2017/0049957, each of which is hereby incorporated herein by reference in its entirety.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display, but may include one or more indicator lights 174 and/or one or more input buttons 172. Pump 102 can also incorporate any or all of the features described with respect to pump 12 in FIG. 2.

Figure 5:
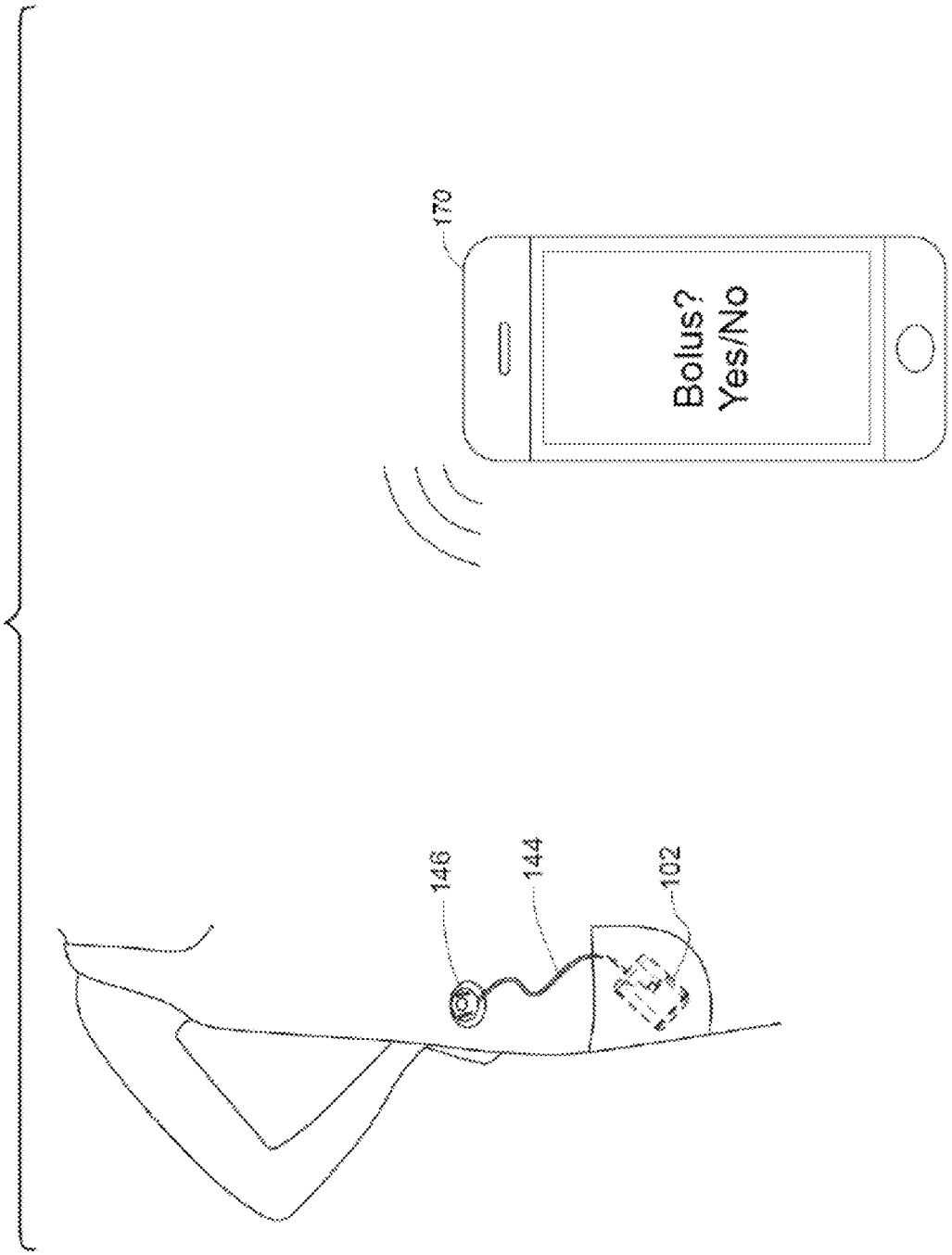
FIG. 5 depicts an embodiment of a pump system according to the disclosure.

As depicted in the embodiment of FIGS. 4A-4B, pump system 100 can include a pump 102 and an infusion set 145. FIG. 4A depicts this infusion set 145 as not connected to pump while FIG. 4B depicts infusion set 145 connected to pump 102 via connectors 154 and 152. Infusion set 145 can include tubing 144 extending between a connector 154 and a site connector 146. Connector 154 can be configured to couple to pump 102 at connector 152 extending from tubing 153. Site connector 146 can be configured to be attached to an infusion site on a user, while pump 102 can be carried in a separate location, such as the user's pocket (as depicted in FIG. 5) or another location on the user's body. Various lengths of tubing 144 can be used in this embodiment to accommodate the user's preference.

Figure 6B:
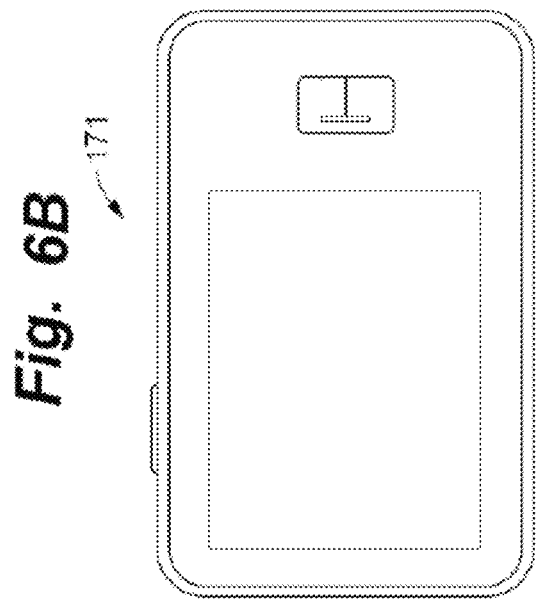
FIGS. 6A-6B depict remote control devices for a pump system according to embodiments of the disclosure.
Figure 6A:
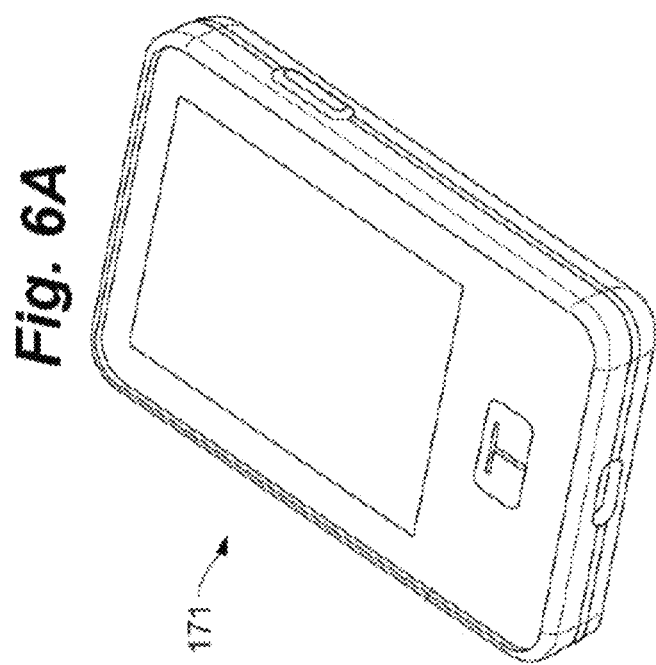

Referring to FIGS. 5-6B, one or more remote control devices 170, 171 can be used to communicate with the processor of pump 12 and/or pump 102 to control delivery of medicament and transfer data with pump via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 5) executing a software application for control of the pump, a dedicated remote controller 171 (as depicted in FIGS. 6A-6B), a wearable electronic watch or electronic health or fitness monitor or personal digital assistant (PDA), etc., or a tablet, laptop or personal computer. Such communications between (and among) the one or more remote control devices 170, 171 and pump 102 may be one-way or two-way for, e.g., effective transfer of data among the devices and the pump, control of pump operations, updating software on the devices and/or pump, and allowing pump-related data to be viewed on the devices and/or pump.

Figure 7:
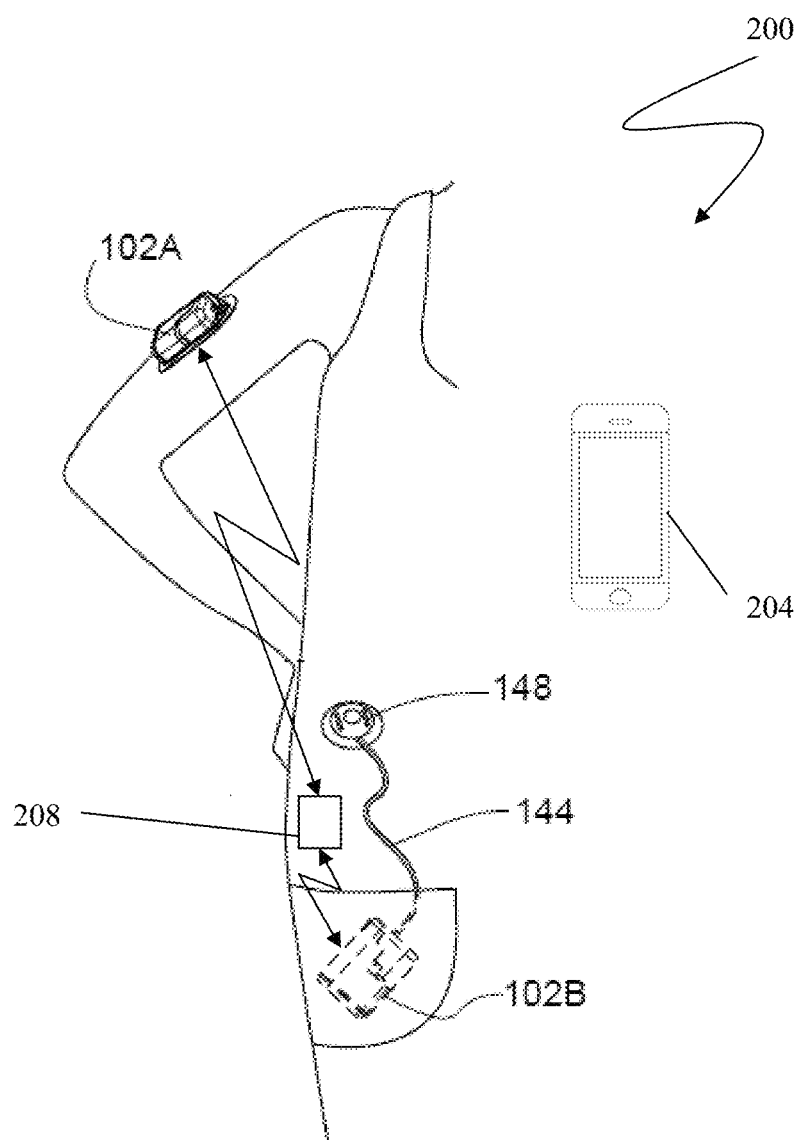
FIG. 7 depicts a schematic representation of a pump system according to an embodiment of the disclosure.

FIG. 7 depicts a schematic representation of a pump system 200 according to an embodiment. System 200 includes a user-wearable infusion pump such as pump 12 or pump 102 described above. In embodiments, a user can alternatively wear the pump 102A directly on the body or place the pump 102B in the user's pocket or other location near the body with infusion tubing 144 extending to an infusion set 148 on the user's body. The system 200 also includes a continuous glucose monitoring (CGM) sensor with a corresponding transmitter 208. The CGM sensor obtains measurements relating to glucose levels in the body and the transmitter communicates that information to the pump 102A/B. The pump 208 can then use the glucose data in making therapy determinations. The system can also include a one or more remote control devices such as a smartphone 204 or other multi-purpose consumer electronic device capable of operating a software application to communicate with and/or control the pump and, alternatively or additionally, a dedicated remote control device designed specifically for use with pump 102A/102B. The smartphone 204 or other remote control device can in some embodiments also be capable of communication with CGM sensor/transmitter 208. In addition, the pump 102A/B and/or smartphone 204 or other remote control device can optionally communicate with additional devices such as, for example, a blood glucose meter or other analyte sensing device, an activity or other health monitor, etc.

Although depicted with the multi-purpose consumer electronic device 204 being a smartphone, in various embodiments the consumer electronic device can alternatively or additional include one or more of a wearable electronic watch, electronic health or fitness monitor, personal digital assistant (PDA), or a tablet, laptop or personal computer, etc. A multi-purpose consumer electronic device can be any device sold to consumers and used for a variety of functions and which can be configured or programmed to communicate with and/or control an infusion pump as one of said functions. In some embodiments, systems as described herein may include more than one multi-purpose consumer electronic device configured for communication with the infusion pump and/or CGM (e.g., a smartphone and an electronic watch).

The devices in the system 200 of FIG. 7 can communicate using any wireless communication modality known in the art. In some embodiments, the devices communicate via Bluetooth. In the embodiment depicted in FIG. 7, Bluetooth communications between the pump 102A/102B and the CGM sensor/transmitter 208 will generally be stable because the devices are positioned relatively close to each other and on generally the same side of the body. However, it is well known that Bluetooth and other radio signals are disrupted and cannot be reliably received through water. Because the human body is primarily comprised of water, Bluetooth signals cannot be reliably transmitted and received through the body. As such, there is a risk in systems such as those depicted in FIG. 7 (in which a CGM sensor/transmitter worn on the body and an infusion pump worn on or in close proximity to the body) that the body could interfere with the Bluetooth signals sending information from the CGM sensor/transmitter to the pump. This signal interference could have significant medical consequences in systems that depend on the CGM data for making proper therapy determinations.

Figure 8:
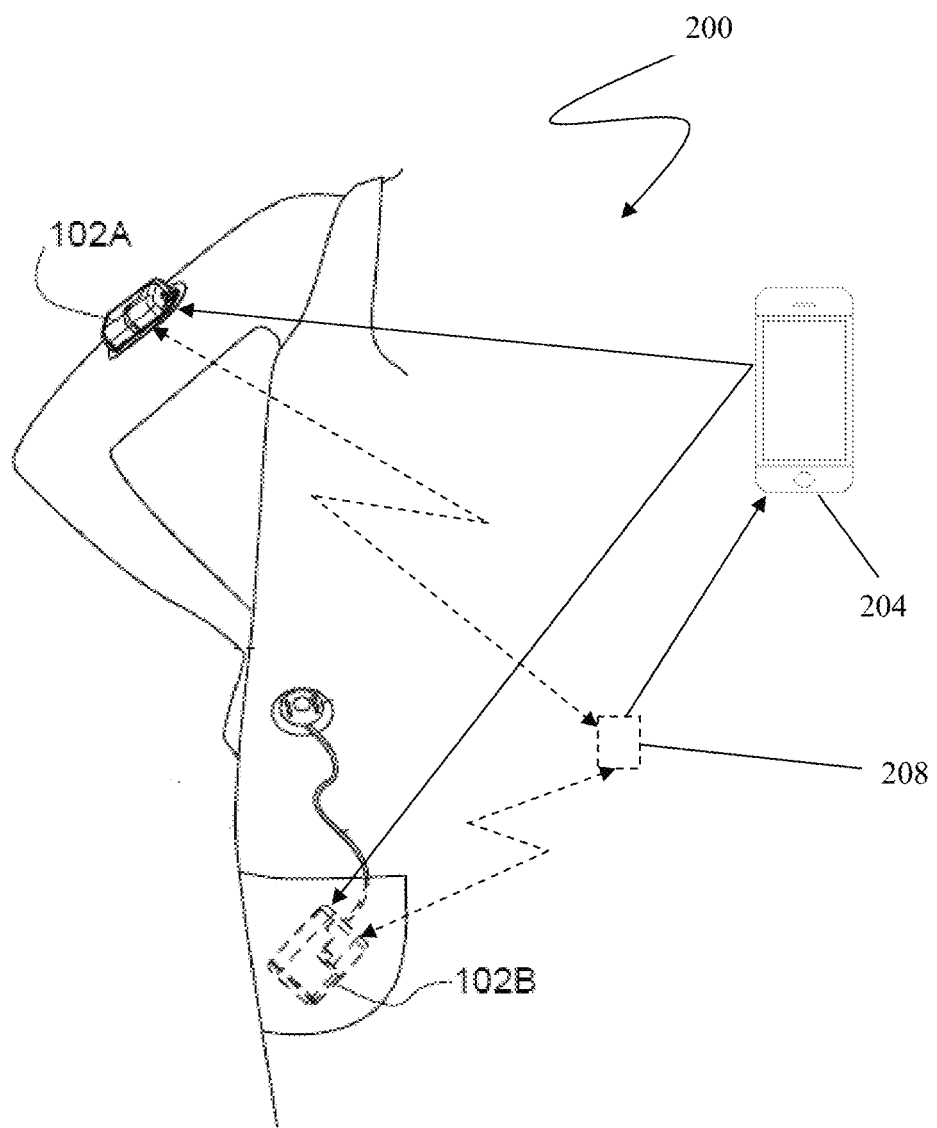
FIG. 8 depicts a schematic representation of a pump system according to an embodiment of the disclosure.

Referring to FIG. 8, an embodiment of a configuration of system 200 in which such signal interference could occur is depicted. In the depicted configuration, the CGM sensor/transmitter 208 is positioned on the rear of the user's body (as indicated by the dashed lines) and on the opposite side of the body from the pump 102A/102B. Because Bluetooth signals cannot reliably be transmitted through the body, it will be difficult for the pump 102A/B to receive a stable signal from the CGM and there may be periods of time where no signal is received.

In a system such as those depicted in FIGS. 7-8 that incorporates a smartphone or other remote control device 204, the remote control device 204 can be employed to remedy any connection issues between the pump and CGM. If the pump 102A/B is not receiving the CGM data from the CGM sensor/transmitter 208, the remote control device 204 can receive the data and then relay the data to the pump 102A/B. In various embodiments, the remote control device 204 can make the determination that the pump is not receiving the data by, for example, 1) the remote control device 204 regularly communicating with the pump 102A/B to ensure the pump is receiving the CGM data, 2) the pump 102A/B notifying the remote control device 204 when the pump is not receiving the data, and/or 3) the CGM sensor/transmitter 208 communicating with the remote control device 204 to notify the remote control that the CGM data is not being received by the pump 102A/B. In various embodiments, the remote control device 204 can communicate with the CGM sensor/transmitter 208 to request the CGM data when the pump is not receiving the data or the CGM sensor/transmitter 208 automatically sends the CGM data to the remote control 204 to relay to the pump 102A/102B. In some embodiments, the remote control 204 may be generally continually receiving the CGM data from the CGM sensor/transmitter 208, but only relays the data to the pump 102A/102B when it is determined that the pump is not receiving the CGM data by one of the aforementioned methods.

CGM data as described herein can include glucose level and trend data that may be used by the pump in making therapy determination, but other data transmitted from the CGM sensor/transmitter to the pump could also be relayed. For example, one or more of diagnostic data such as battery life, sensor performance metrics, sensor algorithm information, therapy or dosing recommendations from the sensor, calibration requests/information, low battery reminders, etc. could also be relayed.

Figure 9:
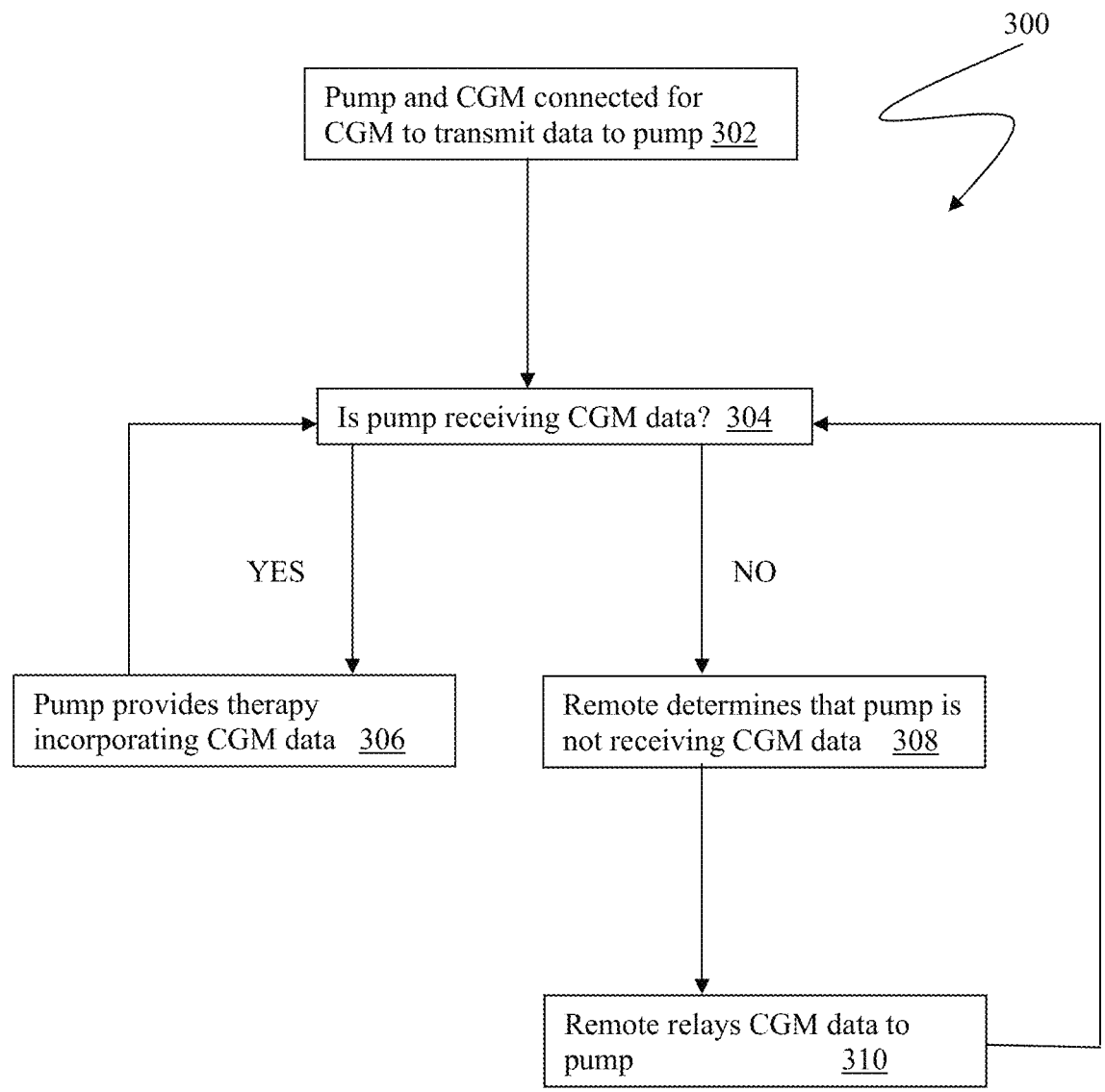
FIG. 9 depicts a flowchart of a method for relaying medical device data according to an embodiment of the disclosure.

FIG. 9 depicts a flowchart of steps in a method 300 for relaying CGM data to a pump according to an embodiment. At step 302, the system is initiated by establishing a wireless connection, such as via Bluetooth, between the pump and the CGM to enable the CGM to transmit data to the pump. At step 304, it is determined whether the pump is receiving CGM data. If the pump is receiving CGM data, at step 306 the pump provides therapy to the patient that incorporates the CGM data. If the pump is not receiving CGM data, the smartphone or other remote device in the system makes a determination that the pump is not receiving data at step 308. As noted above, these determinations can be made with a number of communication protocols including, for example, the pump notifying the remote control that it is not receiving CGM data, the remote control checking with the pump as to whether it is receiving data, the CGM notifying the remote control that the pump is not receiving data, etc. At step 310, the remote control device can then relay the CGM data from the CGM to the pump. As depicted in FIG. 9, these determinations can continually be made at regular intervals. For example, when the remote control is relaying CGM data to the pump, if it determines that the pump subsequently reestablishes the connection with the CGM and is receiving the data, the remote control will revert to steps 304 and 306 and stop relaying the data. In some embodiments, the remote control can alternatively or additionally relay data such as insulin or therapy data from the pump to the CGM.

Although the systems and methods disclosed herein have primarily been described with regard to relaying data to an infusion pump from a CGM sensor/transmitter, the systems and methods herein could be employed with any other type of data intended to be received by an infusion pump and any other type of device configured to communication with an infusion pump. For example, the infusion pump could communicate with various other devices such as, for example, a CGM receiver, a blood glucose meter or other analyte sensing device, an activity or other health monitor, etc. In addition, although primarily described with respect to a smartphone as the relay device, it should be understood than any other device capable of wireless communication with medical devices could be employed as a relay device, such as, for example, a dedicated remote control device, a laptop computer, personal computer, tablet computer, wearable electronic watch or electronic health or fitness monitor, personal digital assistant (PDA), etc. Moreover, the systems and methods described herein are applicable to medical device other than user-wearable infusion pumps.

Although the infusion pump embodiments herein are specifically described primarily with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141, commonly owned U.S. Patent Publication Nos. 2009/0287180; 2012/0123230; 2013/0053816; 2014/0276423; 2014/0276569; 2014/0276570; 2017/0182248; 2017/0250971; 2018/0021514; 2018/0071454; 2019/0240398; 2019/0307952; and 2019/0365997 and commonly owned U.S. patent application Ser. Nos. 16/507,146 and 16/598,343.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

For purposes of interpreting the claims, it is expressly intended that the provisions of 35 U.S.C. § 112(f) are not to be invoked unless the specific terms "means for" or "step for" are recited in a claim.

The invention claimed is:

1. A method of coordinating wireless communications in an infusion pump system including an infusion pump, a remote control device for remotely controlling the infusion pump, and a continuous glucose monitoring system, comprising:
    establishing communications between the infusion pump and the continuous glucose monitoring system to enable the continuous glucose monitoring system to transmit CGM data to the infusion pump;
    determining therapy parameters with the infusion pump utilizing the CGM data;
    determining, by the remote control device, that the infusion pump is no longer receiving the CGM data communicated by the continuous glucose monitoring system;
    receiving the CGM data from the continuous glucose monitoring system at the remote control device only when it has been determined by the remote control device that that the infusion pump is no longer receiving the CGM data; and relaying the CGM data received from the continuous glucose monitoring system from the remote control device to the infusion pump to enable the infusion pump to continue to determine therapy parameters utilizing the CGM data while the infusion pump is no longer receiving the CGM data from the continuous glucose monitoring system;

wherein determining that the infusion pump is no longer receiving the CGM data includes the remote control device communicating with the infusion pump at regular intervals to determine if the infusion pump is receiving the CGM data.

2. The method of claim 1, wherein determining that the infusion pump is no longer receiving the CGM data includes the infusion pump communicating to the remote control device that the infusion pump is no longer receiving the CGM data.

3. The method of claim 1, wherein determining that the infusion pump is no longer receiving the CGM data includes the continuous glucose monitoring system communicating to the remote control device that the infusion pump is no longer receiving the CGM data.

4. The method of claim 1, further comprising relaying with the remote control device communications from the infusion pump to the continuous glucose monitoring system while the infusion pump is no longer receiving the CGM data from the continuous glucose monitoring system.

5. The method of claim 1, further comprising determining that the infusion pump has resumed receiving the CGM data from the continuous glucose monitoring system and ceasing relaying the CGM data from the continuous glucose monitoring system from the remote control device to the infusion pump.

6. The method of claim 1, wherein the remote control device is a dedicated remote control designed for use with the infusion pump.

7. The method of claim 1, wherein the remote control device is a multi-purpose consumer electronic device.

8. The method of claim 1, wherein the remote control device is a smartphone.

9. A method of coordinating wireless communications in an infusion pump system including an infusion pump, a remote control device for remotely controlling the infusion pump, and a continuous glucose monitoring system, comprising:

monitoring, by the remote control device, a connection between the infusion pump and the continuous glucose monitoring system to determine whether the infusion pump is receiving CGM data from the continuous glucose monitoring system;

determining, by the remote control device, that the infusion pump is not receiving the CGM data from the continuous glucose monitoring system;

receiving the CGM data from the continuous glucose monitoring system only when it has been determined the remote control device that the infusion pump is no longer receiving the CGM data; and relaying the CGM data received from the continuous glucose monitoring system to the infusion pump;

wherein determining that the infusion pump is no longer receiving the CGM data includes the remote control device communicating with the infusion pump at regular intervals to determine if the infusion pump is receiving the CGM data.

10. The method of claim 9, wherein monitoring a connection between the infusion pump and the continuous glucose monitoring system includes receiving a communication from the infusion pump indicating that the infusion pump is no longer receiving the CGM data.

11. The method of claim 9, wherein monitoring a connection between the infusion pump and the continuous glucose monitoring system includes receiving a communication from the continuous glucose monitoring system indicating that that the infusion pump is no longer receiving the CGM data.

12. The method of claim 9, further comprising relaying communications from the infusion pump to the continuous glucose monitoring system.

13. The method of claim 9, further comprising determining that the infusion pump has resumed receiving the CGM data from the continuous glucose monitoring system and ceasing relaying the CGM data from the continuous glucose monitoring system to the infusion pump.

14. The method of claim 9, wherein the remote control device is a dedicated remote control designed for use with the infusion pump.

15. The method of claim 9, wherein the remote control device is a multi-purpose consumer electronic device.

16. The method of claim 9, wherein the remote control device is a smartphone.

17. A control device configured to control an infusion pump system including an infusion pump, the control device comprising:

a processor configured to wireless communicate with the infusion pump system and a continuous glucose monitoring system, and execute a plurality of operations associated with controlling the infusion pump such that the processor is configured to:

monitor a connection between the infusion pump and the continuous glucose monitoring system to determine whether the infusion pump is receiving CGM data from the continuous glucose monitoring system;

determine that the infusion pump is not receiving the CGM data from the continuous glucose monitoring system;

receive the CGM data from the continuous glucose monitoring system only when it has been determined that the infusion pump is no longer receiving the CGM data; and relay the CGM data received from the continuous glucose monitoring system to the infusion pump;

wherein determining that the infusion pump is no longer receiving the CGM data includes the remote control device communicating with the infusion pump at regular intervals to determine if the infusion pump is receiving the CGM data.

18. The control device of claim 17, wherein the processor is further configured to determine that the infusion pump has resumed receiving the CGM data from the continuous glucose monitoring system and cease relaying the CGM data from the continuous glucose monitoring system to the infusion pump.

* * * * *